United States Patent
Bonn

(10) Patent No.: US 8,969,722 B2
(45) Date of Patent: *Mar. 3, 2015

(54) THERMALLY TUNED COAXIAL CABLE FOR MICROWAVE ANTENNAS

(75) Inventor: Kenlyn S. Bonn, Lakewood, CO (US)

(73) Assignee: Covidien LP, Mansfield, MA (US)

( * ) Notice: Subject to any disclaimer, the term of this patent is extended or adjusted under 35 U.S.C. 154(b) by 314 days.

This patent is subject to a terminal disclaimer.

(21) Appl. No.: 13/598,141

(22) Filed: Aug. 29, 2012

(65) Prior Publication Data

US 2012/0325516 A1     Dec. 27, 2012

Related U.S. Application Data

(63) Continuation of application No. 12/651,762, filed on Jan. 4, 2010, now Pat. No. 8,258,399, which is a continuation of application No. 12/351,633, filed on Jan. 9, 2009, now Pat. No. 7,642,451.

(60) Provisional application No. 61/023,029, filed on Jan. 23, 2008.

(51) Int. Cl.
*H01B 11/00*     (2006.01)
*H01B 11/18*     (2006.01)
*A61B 17/29*     (2006.01)

(52) U.S. Cl.
CPC ........ *H01B 11/1856* (2013.01); *H01B 11/1873* (2013.01); *A61B 2017/2948* (2013.01)
USPC ................... 174/28; 174/102 R; 174/102 SP; 174/102 P

(58) Field of Classification Search
CPC .............. H01B 3/00; H01B 3/18; H01B 3/20; H01B 3/28; H01B 3/30; H01B 3/301–3/308; H01B 9/00; H01B 9/04; H01B 11/18; H01B 11/1804; H01B 11/1808; H01B 11/1856; H01B 11/186; H01B 11/1886; H01B 11/20
USPC ............ 174/36, 102 R, 102 SP, 102 P, 28, 29, 174/117 AS, 113 AS, 115, 116, 121 R, 113 R, 174/113 C; 333/84 L, 237

See application file for complete search history.

(56) References Cited

U.S. PATENT DOCUMENTS 2,599,857 A * 6/1952 Mildner ........................ 264/145
D223,367 S     4/1972 Kountz (Continued)

FOREIGN PATENT DOCUMENTS

CN     1103807     6/1995
DE      390937     3/1924

(Continued)

OTHER PUBLICATIONS

International Search Report from corresponding European Application No. 09000981.2 mailed Jun. 13, 2013.

(Continued)

*Primary Examiner* — William H Mayo, III

(57) ABSTRACT

A coaxial cable, including an inner conductor and an outer conductor surrounding the inner conductor and a thermally responsive material positioned between the outer conductor and the inner conductor. The outer conductor is in a generally concentric relationship to the inner conductor and the inner and outer conductors are adapted to connect to an energy source. A thermal change in the thermally responsive material alters the generally concentric relationship between the outer conductor and the inner conductor.

12 Claims, 8 Drawing Sheets

(56) References Cited

U.S. PATENT DOCUMENTS

| | | | |
|---|---|---|---|
| 3,761,332 A * | 9/1973 | Jachimowicz et al. | 156/55 |
| 4,011,118 A * | 3/1977 | Geominy | 156/51 |
| 4,018,977 A * | 4/1977 | Herrmann et al. | 174/24 |
| D263,020 S | 2/1982 | Rau, III | |
| D266,842 S | 11/1982 | Villers et al. | |
| D278,306 S | 4/1985 | McIntosh | |
| D295,893 S | 5/1988 | Sharkany et al. | |
| D295,894 S | 5/1988 | Sharkany et al. | |
| 5,262,593 A * | 11/1993 | Madry et al. | 174/102 R |
| 5,344,441 A | 9/1994 | Gronauer | |
| 5,369,251 A | 11/1994 | King et al. | |
| D354,218 S | 1/1995 | Van de Peer | |
| 5,810,803 A | 9/1998 | Moss et al. | |
| 6,026,331 A | 2/2000 | Feldberg et al. | |
| D424,693 S | 5/2000 | Pruter | |
| D424,694 S | 5/2000 | Tetzlaff et al. | |
| D425,201 S | 5/2000 | Tetzlaff et al. | |
| 6,287,302 B1 | 9/2001 | Berube | |
| 6,288,328 B1 | 9/2001 | Brake et al. | |
| D449,886 S | 10/2001 | Tetzlaff et al. | |
| 6,346,671 B1 * | 2/2002 | Ahrens et al. | 174/28 |
| D457,958 S | 5/2002 | Dycus et al. | |
| D457,959 S | 5/2002 | Tetzlaff et al. | |
| 6,527,768 B2 | 3/2003 | Berube | |
| D487,039 S | 2/2004 | Webster et al. | |
| 6,712,644 B1 | 3/2004 | DeCormier | |
| D496,997 S | 10/2004 | Dycus et al. | |
| D499,181 S | 11/2004 | Dycus et al. | |
| 6,812,401 B2 | 11/2004 | Karrmann | |
| 6,849,799 B2 | 2/2005 | Springer et al. | |
| 6,878,147 B2 | 4/2005 | Prakash et al. | |
| 6,956,164 B2 | 10/2005 | Brown | |
| D525,361 S | 7/2006 | Hushka | |
| D531,311 S | 10/2006 | Guerra et al. | |
| D533,942 S | 12/2006 | Kerr et al. | |
| 7,147,632 B2 | 12/2006 | Prakash et al. | |
| D535,027 S | 1/2007 | James et al. | |
| 7,194,297 B2 | 3/2007 | Talpade et al. | |
| D541,418 S | 4/2007 | Schechter et al. | |
| D541,938 S | 5/2007 | Kerr et al | |
| 7,244,254 B2 | 7/2007 | Brace et al. | |
| 7,311,703 B2 | 12/2007 | Turovskiy et al. | |
| D564,662 S | 3/2008 | Moses et al. | |
| D576,932 S | 9/2008 | Strehler | |
| 7,525,041 B2 | 4/2009 | Howard et al. | |
| D594,736 S | 6/2009 | Esjunin | |
| D594,737 S | 6/2009 | Kelly et al. | |
| D606,203 S | 12/2009 | Husheer et al. | |
| 7,674,981 B1 | 3/2010 | Hesselbarth et al. | |
| D613,412 S | 4/2010 | DeCarlo | |
| D634,010 S | 3/2011 | DeCarlo | |
| 8,133,222 B2 | 3/2012 | Ormsby | |
| 2008/0234574 A1 | 9/2008 | Hancock et al. | |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10310765 | 9/2004 |
| DE | 10328514 | 3/2005 |
| DE | 102004022206 | 12/2005 |
| DE | 202005015147 | 3/2006 |
| DE | 102009015699 | 5/2010 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 0 882 955 | 12/1998 |
| EP | 1 159 926 | 5/2001 |
| EP | 0 648 515 | 4/2003 |
| FR | 179 607 | 11/1906 |
| FR | 1 275 415 | 10/1961 |
| FR | 1 347 865 | 11/1963 |
| FR | 2 235 669 | 1/1975 |
| FR | 2 276 027 | 1/1976 |
| FR | 2 313 708 | 12/1976 |
| FR | 2 502 935 | 10/1982 |
| FR | 2 517 953 | 6/1983 |
| FR | 2 573 301 | 5/1986 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09000492 | 1/1997 |
| JP | 09010223 | 1/1997 |
| JP | 11244298 | 9/1999 |
| JP | 2000342599 | 12/2000 |
| JP | 2000350732 | 12/2000 |
| JP | 2001003776 | 1/2001 |
| JP | 2001008944 | 1/2001 |
| JP | 2001029356 | 2/2001 |
| JP | 2001037775 | 2/2001 |
| JP | 2001128990 | 5/2001 |
| JP | 2001231870 | 8/2001 |
| JP | 2008142467 | 6/2008 |
| SU | 166452 | 11/1964 |
| SU | 401367 | 11/1974 |
| SU | 727201 | 4/1980 |
| WO | WO00/36985 | 6/2000 |
| WO | 2007024878 A1 | 3/2007 |
| WO | 2007112081 A1 | 10/2007 |
| WO | 2008008545 A2 | 1/2008 |
| WO | WO2010/035831 | 4/2010 |

OTHER PUBLICATIONS

U.S. Appl. No. 08/136,098, filed Oct. 14, 1993, Roger A. Stern.
U.S. Appl. No. 08/483,742, filed Jun. 7, 1995, Roger A. Stern.
U.S. Appl. No. 13/050,729, filed Mar. 17, 2011, Casey M. Ladtkow.
U.S. Appl. No. 13/083,185, filed Apr. 8, 2011, Arnold V. DeCarlo.
U.S. Appl. No. 13/083,256, filed Apr. 8, 2011, Joseph D. Brannan.
U.S. Appl. No. 13/113,736, filed May 23, 2011, Ladtkow et al.

(56) References Cited

OTHER PUBLICATIONS

U.S. Appl. No. 13/118,929, filed May 31, 2011, Bonn et al.
U.S. Appl. No. 13/206,075, filed Aug. 9, 2011, Lee et al.
U.S. Appl. No. 13/236,997, filed Sep. 20, 2011, Behnke, II et al.
U.S. Appl. No. 13/237,068, filed Sep. 20, 2011, Behnke, II et al.
U.S. Appl. No. 13/237,187, filed Sep. 20, 2011, Behnke, II et al.
U.S. Appl. No. 13/237,342, filed Sep. 20, 2011, Behnke, II et al.
U.S. Appl. No. 13/237,488, filed Sep. 20, 2011, Behnke, II et al.
U.S. Appl. No. 13/343,788, filed Jan. 5, 2012, William O. Reid, Jr.
U.S. Appl. No. 13/343,798, filed Jan. 5, 2012, William O. Reid, Jr.
U.S. Appl. No. 13/344,753, filed Jan. 6, 2012, Lee et al.
U.S. Appl. No. 13/344,790, filed Jan. 6, 2012, Lee et al.
U.S. Appl. No. 13/400,223, filed Feb. 20, 2012, Anthony B. Ross.
U.S. Appl. No. 13/419,981, filed Mar. 14, 2012, Joseph D. Brannan.
U.S. Appl. No. 13/430,810, filed Mar. 27, 2012, Joseph D. Brannan.
U.S. Appl. No. 13/440,690, filed Apr. 5, 2012, Joseph D. Brannan.
U.S. Appl. No. 13/460,440, filed Apr. 30, 2012, Arnold V. DeCarlo.
U.S. Appl. No. 13/464,021, filed May 4, 2012, Joseph D. Brannan.
U.S. Appl. No. 13/477,260, filed May 22, 2012, William R. Reid, Jr.
U.S. Appl. No. 13/477,307, filed May 22, 2012, Casey M. Ladtkow.
U.S. Appl. No. 13/477,320, filed May 22, 2012, Joseph D. Brannan.
U.S. Appl. No. 13/483,858, filed May 30, 2012, Francesca Rossetto.
U.S. Appl. No. 13/488,964, filed Jun. 5, 2012, Steven P. Buysse.
U.S. Appl. No. 13/525,853, filed Jun. 18, 2012, Joseph A. Paulus.
U.S. Appl. No. 13/526,676, filed Jun. 19, 2012, Francesca Rossetto.
U.S. Appl. No. 13/539,650, filed Jul. 2, 2012, Joseph A. Paulus.
U.S. Appl. No. 13/539,690, filed Jul. 2, 2012, Steven P. Buysse.
U.S. Appl. No. 13/539,725, filed Jul. 2, 2012, Steven P. Buysse.
U.S. Appl. No. 13/539,875, filed Jul. 2, 2012, Mani N. Prakash.
U.S. Appl. No. 13/551,005, filed Jul. 17, 2012, Chris Rusin.
U.S. Appl. No. 13/567,624, filed Aug. 6, 2012, Mani N. Prakash.
U.S. Appl. No. 13/568,679, filed Aug. 7, 2012, Robert J. Behnke, II.
U.S. Appl. No. 13/596,785, filed Aug. 28, 2012, Richard A. Willyard.
U.S. Appl. No. 13/598,141, filed Aug. 29, 2012, Kenlyn S. Bonn.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic ® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division. (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw Hill, vol. 111, (1984), pp. 2490-2499.
Cosman et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" Advanced Input Systems, located at: <http://www.advanced-input.com/lightkey> 2002.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Humphries Jr. et al., "Finite•Element Codes to Model Electrical Heating and Non•Llnear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.

(56) References Cited

OTHER PUBLICATIONS

Jarrett et al., "Use of the LigaSure™ Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol., BME-31, No. 1, Jan. 1984, pp. 28-37.
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology. p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.

Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/1977).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157
"Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl I ):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001)71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817-825.
Urologix, Inc.-Medical Professionals: Targis™ Technology (Date Unknown). "Overcoming the Challenge" located at: <http://www.urologix.com!medicaUtechnology.html > Nov. 18, 1999; 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.

(56) References Cited

OTHER PUBLICATIONS

W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Aug. 4, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2008.
European Search Report EP 07015601.3 dated Jan. 4, 2008.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001016.8 dated Jan. 4, 2008.
European Search Report EP 08001019 dated Sep. 23, 2008.
European Search Report EP 08004974.5 dated Apr. 6, 2011.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08007924.7 partial dated Aug. 17, 2010.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09012389.4 dated Jul. 6, 2010.
European Search Report EP 09151621 dated Jun. 18, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.
European Search Report EP 09172838.6 extended dated Jan. 20, 2010.
European Search Report EP 09173268.5 extended dated Jan. 27, 2010.

(56) References Cited

OTHER PUBLICATIONS

European Search Report EP 09704429.1 extended dated Mar. 23, 2011.
European Search Report EP 10001767.2 extended dated Jun. 18, 2010.
European Search Report EP 10004950.1 extended dated Jul. 2, 2010.
European Search Report EP 10004951.9 extended dated Jul. 2, 2010.
European Search Report EP 10005533.4 extended dated Sep. 24, 2010.
European Search Report EP 10005534.2 extended dated Sep. 17, 2010.
European Search Report EP 10006373.4 extended dated Oct. 11, 2010.
European Search Report EP 10008139.7 extended dated Nov. 30, 2010.
European Search Report EP 10008140.5 extended dated Dec. 28, 2010.
European Search Report EP 10008533.1 extended dated Dec. 20, 2010.
European Search Report EP 10008850.9 extended dated Nov. 30, 2010.
European Search Report EP 10009392.1 extended dated Sep. 19, 2011.
European Search Report EP 10009731.0 extended dated Jan. 28, 2011.
European Search Report EP 10009732.8 extended dated Jan. 26, 2011.
European Search Report EP 10010943.8 extended dated Feb. 1, 2011.
European Search Report EP 10011750.6 extended dated Feb. 1, 2011.
European Search Report EP 10014042.5 extended dated Feb. 18, 2011.
European Search Report EP 10014080.5 extended dated Mar. 17, 2011.
European Search Report EP 10014081.3 extended dated Mar. 17, 2011.
European Search Report EP 10014705.7 extended dated Apr. 27, 2011.
European Search Report EP 10158944.8 extended dated Jun. 21, 2010.
European Search Report EP 10161596.1 extended dated Jul. 28, 2010.
European Search Report EP 10161722.3 extended dated Jun. 16, 2010.
European Search Report EP 10163235.4 dated Aug. 10, 2010.
European Search Report EP 10172634.7 dated Nov. 9, 2010.
European Search Report EP 10185413.1 dated Dec. 7, 2010.
European Search Report EP 10185413.1 dated Mar. 14, 2011.
European Search Report EP 10191321.8 dated Apr. 7, 2011.
European Search Report EP 11000548.5 extended dated Apr. 14, 2011.
European Search Report EP 11000669.9 extended dated Jun. 30, 2011.
European Search Report EP 11001596.3 extended dated Jul. 4, 2011.
European Search Report EP 11001872.8 extended dated Jul. 6, 2011.
European Search Report EP 11004942 dated Oct. 4, 2011.
European Search Report EP 11009036.2 dated Feb. 13, 2012.
European Search Report EP 11010024.5 dated Apr. 20, 2012.
European Search Report EP 11010046.8 dated Apr. 17, 2012.
European Search Report EP 11010093.0 dated Mar. 27, 2012.
European Search Report EP 11010175.5 dated May 10, 2012.
European Search Report EP 11010176.3 dated Apr. 2, 2012.
European Search Report EP 11010177.1 dated May 10, 2012.
European Search Report EP 11174318.3 dated Nov. 7, 2011.
European Search Report EP 11185926.0 dated Feb. 3, 2012.
European Search Report EP 12000334.8 dated May 4, 2012.
European Search Report EP 12000335.5 dated May 10, 2012.
European Search Report EP 12000336.3 dated May 14, 2012.
European Search Report EP 12001841.1 dated Jul. 16, 2012.
International Search Report PCT/US97/05066 dated Jun. 24, 1997.
International Search Report PCT/US98/18640 dated Jan. 29, 1999.
International Search Report PCT/US98/23950 dated Jan. 14, 1999.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2005.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report PCT/US10/032796 dated Jul. 28, 2010.

* cited by examiner

THERMALLY TUNED COAXIAL CABLE FOR MICROWAVE ANTENNAS

CROSS-REFERENCE TO RELATED APPLICATIONS

This application is a continuation application of U.S. patent application Ser. No. 12/651,762, filed on Jan. 4, 2010, now U.S. Pat. No. 8,258,399, which is a continuation application of U.S. patent application Ser. No. 12/351,633, filed on Jan. 9, 2009, now U.S. Pat. No. 7,642,451, which claims the benefit of priority to U.S. Provisional Patent Application Ser. No. 61/023,029, titled "THERMALLY TUNED COAXIAL CABLE FOR MICROWAVE ANTENNAS" filed Jan. 23, 2008 by Kenlyn Bonn, all of which are incorporated by reference herein.

BACKGROUND

1. Technical Field

The present disclosure relates generally to microwave antennas. More particularly, the present disclosure relates to thermally tuning coaxial cables for microwave antennas.

2. Background of Related Art

Microwave antennas are used in many applications. For example, medical microwave ablation antennas are used by surgeons. In fact, ablation devices utilizing DC shock, radio frequency (RF) current, ultrasound, microwave, direct heat, or lasers have been introduced and employed to various degrees to ablate biological tissues. Ablation devices may be used in open surgical procedures or are sometimes inserted into catheter devices in order to perform laparoscopic ablation procedures. The catheter incorporating the ablation device is generally inserted into a major vein or artery or through a body cavity. These catheters are then guided to a targeted location in the body (e.g., organ) by manipulating the catheter from the insertion point or the natural body orifice.

During ablation, the dielectric constant of the tissue changes as more water is boiled off and tissue desiccation occurs. The changing value of the dielectric constant alters the antenna's ability to match the originally designed impedance of the antenna. In addition, during microwave ablation in tissue, the impedance of the tissue varies during the course of ablation. This occurrence directly corresponds to how much energy has been deposited into the tissue during the ablation, resulting in temperature increases at the ablation site.

The impedance in the coaxial cable is typically related to the concentricity of the inner conductor in relationship to the outer conductor. In ablation procedures, however, conventional antenna designs only allow for an initial impedance match and as ablation occurs, the increase in mismatch between the tuning point of the antenna and the ablated tissue reduces the efficiency of the energy deposition in the tissue.

SUMMARY

The present disclosure relates to a coaxial cable. The coaxial cable includes an inner conductor and an outer conductor surrounding the inner conductor configured in a generally concentric relationship therewith, the inner and outer conductors adapted to connect to an energy source. A thermally responsive material is positioned between the outer conductor and the inner conductor wherein a thermal change in the thermally responsive material alters the generally concentric relationship between the outer conductor and the inner conductor.

The thermally responsive material of the coaxial cable may include first and second dielectric materials wherein the first dielectric material has a first coefficient of thermal expansion and the second dielectric material has a second coefficient of thermal expansion different from the first coefficient of thermal expansion.

In another embodiment, the thermally responsive material of the coaxial cable may include a first resistive heating element at least partially disposed in the first dielectric material and a second resistive heating element at least partially disposed in the second dielectric material. A thermal change may be defined by the application of heat via one or more of the first and the second resistive heating elements.

In yet another embodiment, the thermally responsive material further includes a first dielectric material that surrounds the inner conductor and a plurality of resistive heating elements disposed in the first dielectric material and substantially parallel to the inner conductor along a length of the coaxial cable. A thermal change may be defined by the application of heat to the first dielectric material via the one or more of the plurality of resistive heating elements.

In yet another embodiment, the coaxial cable includes a sensor that monitors the inner conductor and/or the outer conductor for determining a position of the inner conductor relative to the outer conductor.

In still yet another embodiment, the thermally responsive material of the coaxial cable includes a shape memory alloy responsive to changes in temperature and the thermal change in the shape memory alloy alters the generally concentric relationship between the outer conductor and the inner conductor.

In another embodiment, the thermally responsive material of the coaxial cable also includes one or more dielectric spacer(s) in a longitudinally-spaced apart relationship with respect to each other. Each of the dielectric spacer(s) includes a coefficient of thermal expansion wherein the thermal change of the thermally responsive material alters the generally concentric relationship between the outer conductor and the inner conductor at each of the plurality of spacers. The coefficient of thermal expansion of each of the plurality of spacers may not be equal.

The spacers may further include a first spacer with a first dielectric material and a first coefficient of thermal expansion and a second spacer with a second dielectric material and a second coefficient of thermal expansion. The first dielectric material and the second dielectric material may be different materials. The plurality of spacers may be in a spaced apart relationship with respect to each other.

The present disclosure also relates to a coaxial cable that includes an inner conductor and an outer conductor surrounding the inner conductor, the inner and outer conductors adapted to connect to an energy source. A first dielectric material is disposed between the inner conductor and the outer conductor, the first dielectric material having a first fluid conduit defined therein. A second dielectric material is disposed between the inner conductor and the outer conductor, the second dielectric material having a second fluid conduit defined therein. The first dielectric material and the second dielectric materials are configured to position the inner conductor in a generally concentric relationship relative to the outer conductor and are formed of thermally responsive materials wherein a change in temperature of the first or the second dielectric material alters the generally concentric relationship between the inner conductor and the outer conductor. Fluid provided to the first fluid conduit and/or the second fluid conduit defines the change in temperature and is selectively controllable to regulate the thermal expansion of the thermally responsive material.

The present disclosure also relates to a surgical device including an inner conductor, an outer conductor surrounding the inner conductor configured in a generally concentric relationship therewith. An ablative energy delivery device is adapted to couple to an ablative energy source, through the inner and outer conductors, to deliver energy to tissue. A thermally responsive material is positioned between the outer conductor and the inner conductor wherein a thermal change in the thermally responsive material alters the generally concentric relationship between the outer conductor and the inner conductor.

The thermally responsive material selectively aligns or misaligns the inner conductor relative to the outer conductor for tuning and impedance matching. The thermally responsive material may position the inner conductor relative to the outer conductor from a first position wherein the inner conductor is concentrically-aligned with the outer conductor to a second position wherein the inner conductor is not concentrically-aligned with the outer conductor.

BRIEF DESCRIPTION OF THE DRAWINGS

Various embodiments of the present disclosure are described herein with reference to the drawings wherein.

DETAILED DESCRIPTION

Figure 1A:
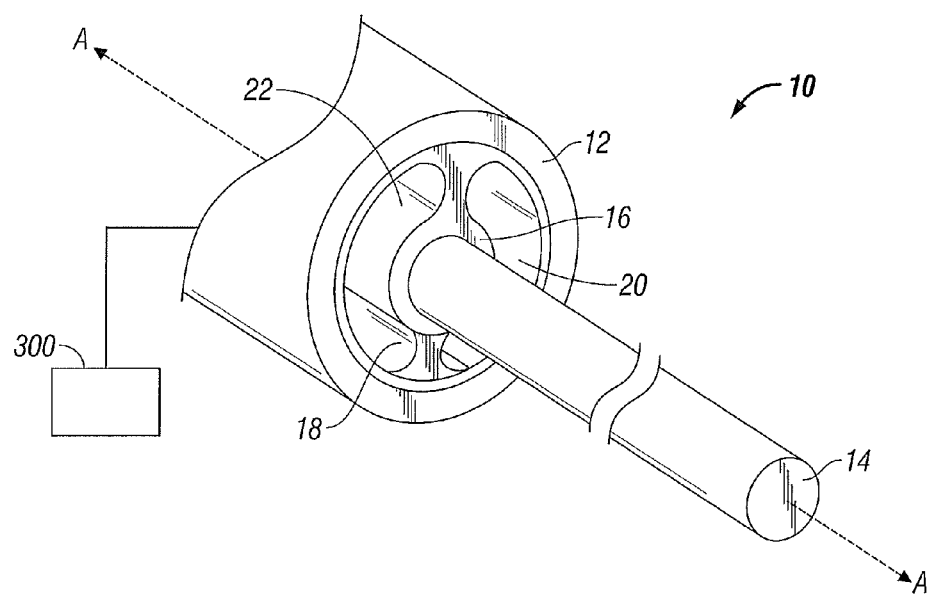
FIG. 1A is a front, perspective view of a centrally-disposed coaxial cable having an inner conductor held by two materials having different coefficient of thermal expansion values, in accordance with an embodiment of the present disclosure.

To achieve the foregoing and other objects of the present disclosure, methods and devices pertaining to the microwave antennas are disclosed. In general, the present disclosure pertains to a coaxial cable assembly and, in one embodiment, to a surgical device including the coaxial cable assembly. The surgical device generally includes an ablative energy source and an ablative energy delivery device coupled to the ablative energy source. The ablative energy delivery device is configured to deliver ablative energy sufficiently strong enough to cause tissue ablation. In most embodiments, the ablative energy is formed from electromagnetic energy in the microwave frequency range. Other applications are contemplated by the present disclosure, such as telecommunications or other suitable applications in which microwave antennas are utilized.

Particular embodiments of the present disclosure are described hereinbelow with reference to the accompanying drawings. In the following description, well-known functions or constructions are not described in detail to avoid obscuring the present disclosure in unnecessary detail. Those skilled in the art will understand that the present disclosure may be adapted for use with either an endoscopic instrument or an open instrument.

While the present disclosure is susceptible to embodiments in many different forms, there is shown in the drawings and will be described herein in detail one or more embodiments of the present disclosure. However, the present disclosure is to be considered an exemplification of the principles of the present disclosure, and the embodiment(s) illustrated is/are not intended to limit the spirit and scope of the present disclosure and/or the claims herein.

With reference to the drawings, the coaxial cable of the particular embodiments of the present disclosure are shown. The cable may be of any suitable length, and the figures are not intended to limit the length of the cable to a specific length illustrated or any specific length. Instead, only a representative portion or section of cable is illustrated.

Figure 1B:
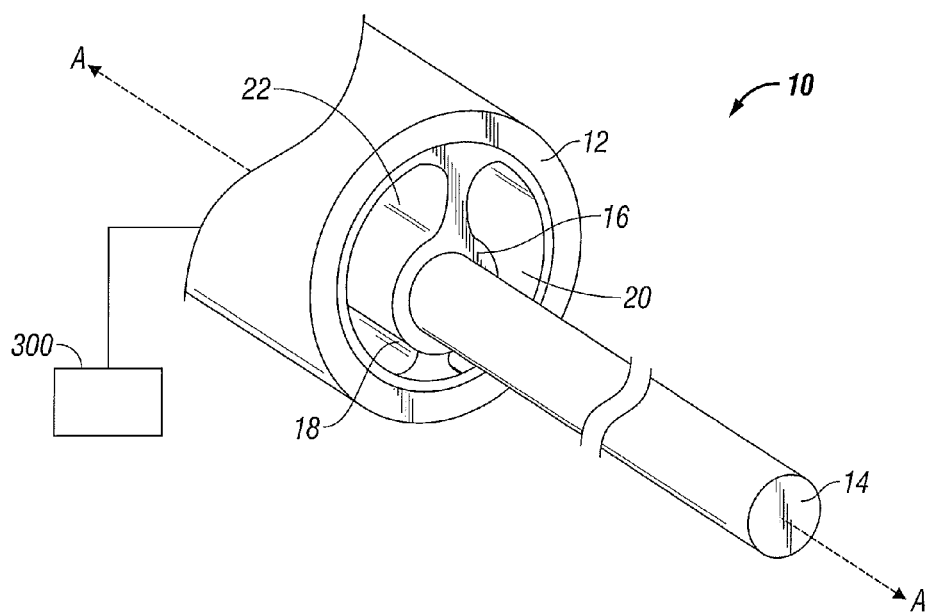
FIG. 1B is a front, perspective view of an off-center coaxial cable having an inner conductor held by two materials having different coefficient of thermal expansion values, in accordance with another embodiment of the present disclosure.

Referring to the embodiment of FIGS. 1A and 1B, the coaxial cable 10 includes an outer conductor 12, an inner conductor 14, a first material 16, a second material 18, a first air gap 20, and a second air gap 22. The inner conductor 14 is connected to an external power source 300.

The coaxial cable 10 may be rigid, rigid-but shapeable or flexible. The coaxial cable 10 may be chosen from commercially available standards and is generally designed with a characteristic impedance of 50 Ohms. In addition, one side of the coaxial cable 10 may be coupled to a power supply 300. Also, the other side of the coaxial cable 10 may be coupled to an antenna (not shown) in any suitable manner.

The outer conductor 12 is arranged to be generally concentric with respect to the inner conductor 14. However, the concentric relationship may be configured to meet a particular purpose as explained in more detail below. Inner conductor 14 is a central conductor used for transmitting signals and is typically held relative to the outer conductor 12 by first material 16 and second material 18. In one embodiment, the first material 16 holds the inner conductor 14, whereas the second material 18 supports the first material 16 without contacting the inner conductor 14. In other words, only one material contacts the inner conductor 14.

In the illustrated embodiment, the first material 16 and the second material 18 define first and second air gaps 20, 22 between the inner surface of the outer conductor 12 and the outer surface of the inner conductor 14. The first air gap 20 separates a first portion of the first material 16 and a first portion of the second material 18. The second air gap 22 separates a second portion of the first material 16 with a second portion of the second material 18.

The inner conductor 14 has a significant effect on the coaxial cable's 10 properties, such as the cable's 10 impedance and attenuation characteristics. The impedance on the coaxial cable 10 is related to the concentricity of the inner conductor 14 in relationship to the outer conductor 12. In the first embodiment, a thermal increase to the coaxial cable 10 is used to alter the alignment concentricity of the inner conductor 14 in a manner that would better match a change in tissue impedance. The coaxial cable 10 in the antenna (not shown) would start with an initial impedance match to a transmission line interface that would gradually taper along the length of the antenna toward a desired impedance with either the addition or the subtraction of heat. The taper could be controlled thermally through additional features, such as a cooling jacket or cooling channels.

Figure 1C:
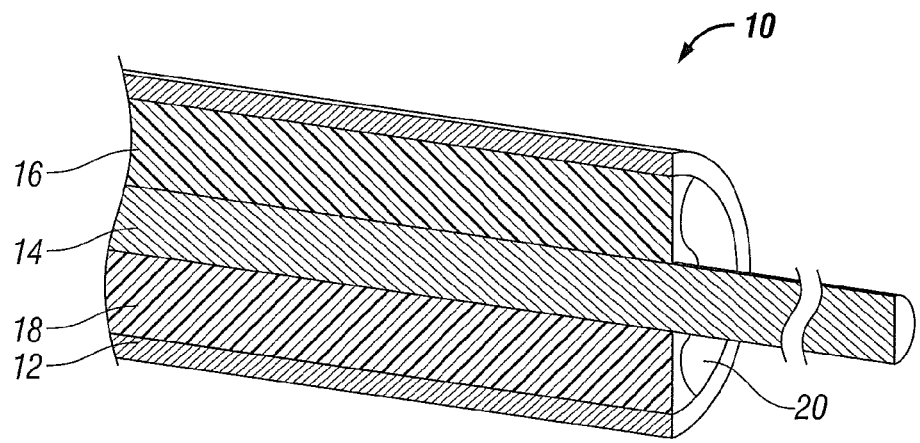
FIG. 1C is a schematically-illustrated, cross-sectional view of the coaxial cable of FIG. 1A.
Figure 1D:
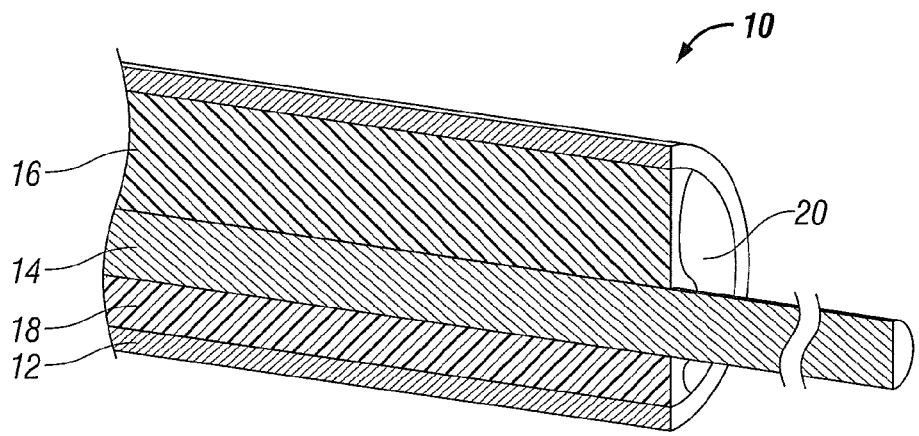
FIG. 1D is a schematically-illustrated, cross-sectional view of the coaxial cable of FIG. 1B.

FIGS. 1A and 1C illustrate the inner conductor 14 in a centered position within the coaxial cable 10. As heat is applied, the inner conductor 14 is moved to an off-centered position due to the thermal expansion of material 18, as shown in FIGS. 1B and 1D. As the tissue impedance changes, the alignment sensitivity of the cable 10 may be selectively changed (e.g., automatically or manually) such that the impedance of the cable 10 better matches the tissue impedance. One or more materials with different coefficients of thermal expansion may be utilized which mutually cooperate to tune the inner conductor 14 according to a desired setting, such as an ohmage setting.

Figure 2A:
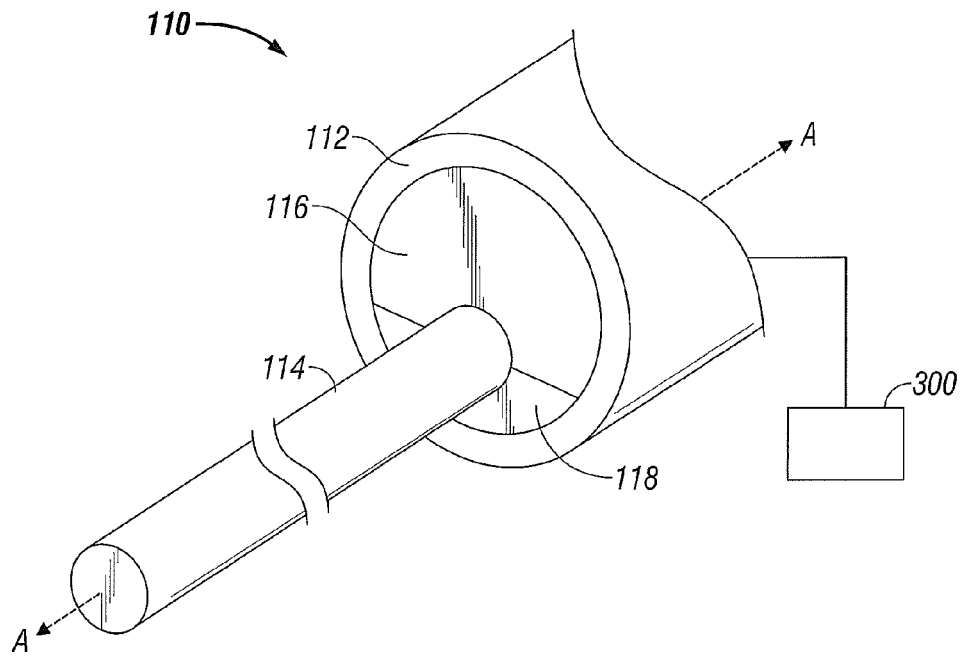
FIG. 2A is front, perspective view of an off-centered coaxial cable having an inner conductor held by two materials having different coefficient of thermal expansion values, in accordance with another embodiment of the present disclosure.
Figure 2B:
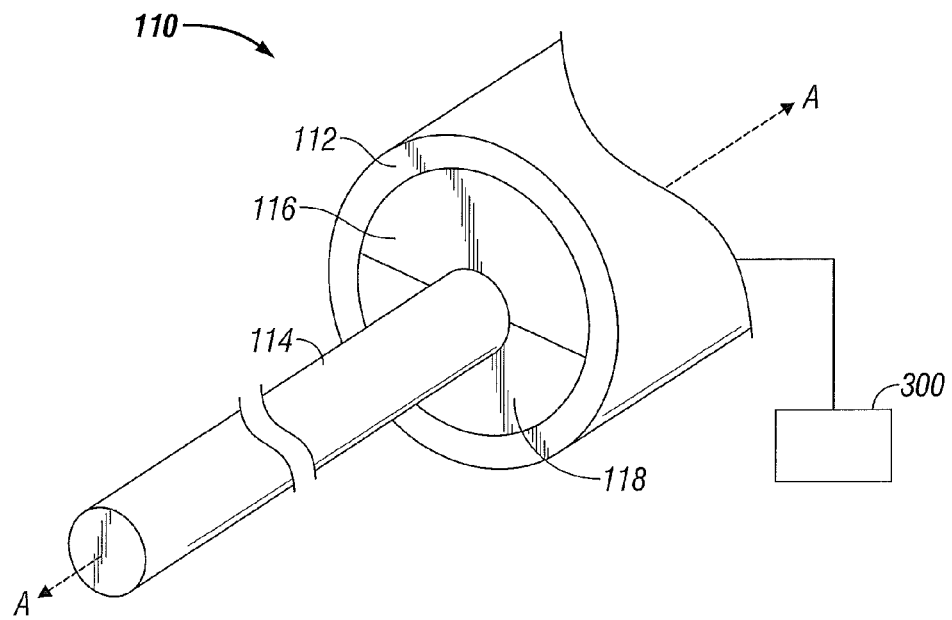
FIG. 2B is a front, perspective view of a centrally disposed coaxial cable having an inner conductor held by two materials having different coefficient of thermal expansion values, in accordance with another embodiment of the present disclosure.
Figure 2C:
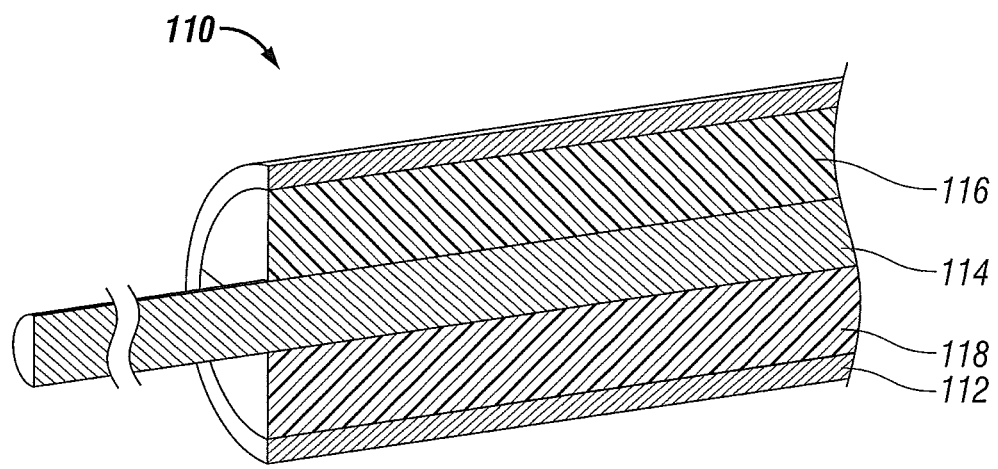
FIG. 2C is a schematically-illustrated, cross-sectional view of the coaxial cable of FIG. 2B.
Figure 2D:
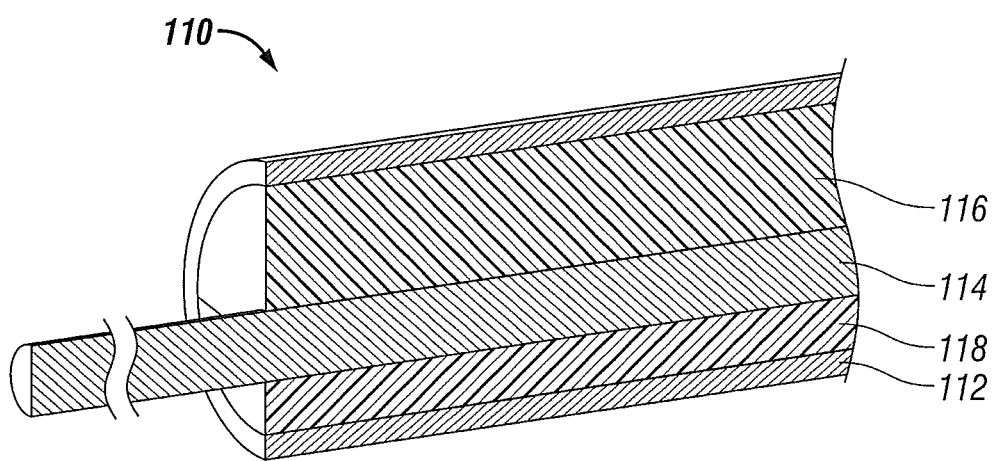
FIG. 2D is a schematically-illustrated, cross-sectional view of the coaxial cable of FIG. 2A.

FIGS. 2A and 2D show an off-centered coaxial cable 110 and FIGS. 2B and 2C show a centrally disposed coaxial cable 110 having an inner conductor held by two materials having different coefficient of thermal expansion values. The coaxial cable 110 includes an outer conductor 112, an inner conductor 114, a first material 116 and a second material 118. The inner conductor 114 is connected to an external power source 300.

The first material 116 has a first coefficient of thermal expansion value and the second material 118 has a second coefficient of thermal expansion value, the first and second coefficient of thermal expansion values being different. During heat transfer, the energy that is stored in the intermolecular bonds between atoms changes. When the stored energy increases, so does the length of the molecular bond. As a result, materials typically expand in response to heating and contract on cooling. This response to temperature change is expressed as the materials coefficient of thermal expansion. The coefficient of thermal expansion is used in two ways: (1) as a volumetric thermal expansion coefficient and (2) as a linear thermal expansion coefficient.

Therefore, when the temperature applied to the coaxial cable 110 changes, the first material 116 expands at a first rate/volume and the second material 118 expands at a second rate/volume. Typical materials used in coaxial cables include variations of PTFE, polyethylene (PE) blends and silica dioxides, however, nearly any thermo-set or thermoplastic with a low dielectric constant can be used in conjunction with another material of similar dielectric constant with a different coefficient of thermo-expansion. Typically, different polymer grades or blends result in varying material properties so determining the desired pair of materials would be a result of finding a matching mixture. The heat generated by the losses in the dielectric material in the cable can also be utilized to heat material enough to generate the differential in thermal expansion between the varying materials. A variety of different materials with different coefficient of thermal expansion values may be utilized, e.g., ABS Polymer Extruded, ABS Polymer Nylon Blend, PEEK Polyketone, PEKK Polyketone, Nylon PTFE Filled, Polycarbonate Extruded, LDPE (Polyethylene), Polyimide, PTFE Molded, Silica Aerogel and combinations thereof.

If the first material 116 expands due to a temperature increase, the second material 118 contracts due to the differing coefficient of thermal expansion values of the two materials 116, 118. As a result, as the ablation zone heats up, the difference in expansion between the two materials 116, 118 would cause the inner conductor 114 to change alignment with the outer conductor 112, e.g., move toward a centered position as illustrated in FIGS. 2B and 2C.

As can be appreciated, the materials 116, 118 may be designed to selectively (e.g., either automatically or manually) align or misalign the inner conductor 114 relative to the outer conductor 112 for tuning and impedance matching purposes. In the embodiment, as seen in FIGS. 1A and 1B, the design could be made to start with the inner conductor 114 concentrically centered relative to outer conductor 112 and then moved off center when the temperature changes. As shown in FIGS. 2A and 2B, inner conductor 114 may be normally off-center relative to outer conductor 112, and as the temperature increases, the inner conductor 114 moves toward the concentric center of the coaxial cable 110 when one of the materials 116, 118 is heated.

The system described in regard to FIGS. 1A-2B may include an electrosurgical generator 300 having a microprocessor and sensor circuitry (not shown) that continually monitors tissue impedance and measures offset impedance. The sensor circuitry may also continually monitor the position of the inner conductor 114 of a coaxial cable 110 with respect to a desired coaxial position (e.g., a center position). The monitor may be operably coupled to a mechanism (shape memory alloy, heat resistive element) as explained in more detail below) for regulating the thermal expansion of at least one of the first and second dielectric materials 116, 118 to position the inner conductor 114 relative to the outer conductor 112 to change the impedance of the inner conductor 114. The microprocessor or the circuitry may also be configured to compare the inner conductor positioning to a predetermined center position. If the inner conductor is positioned above or below the predetermined center position, one or more materials 116, 118 surrounding the inner conductor are heated or moved to re-position the inner conductor 114 to a desired position, and the microprocessor reports such findings to a user control or maintains this data for subsequent use.

Figure 3:
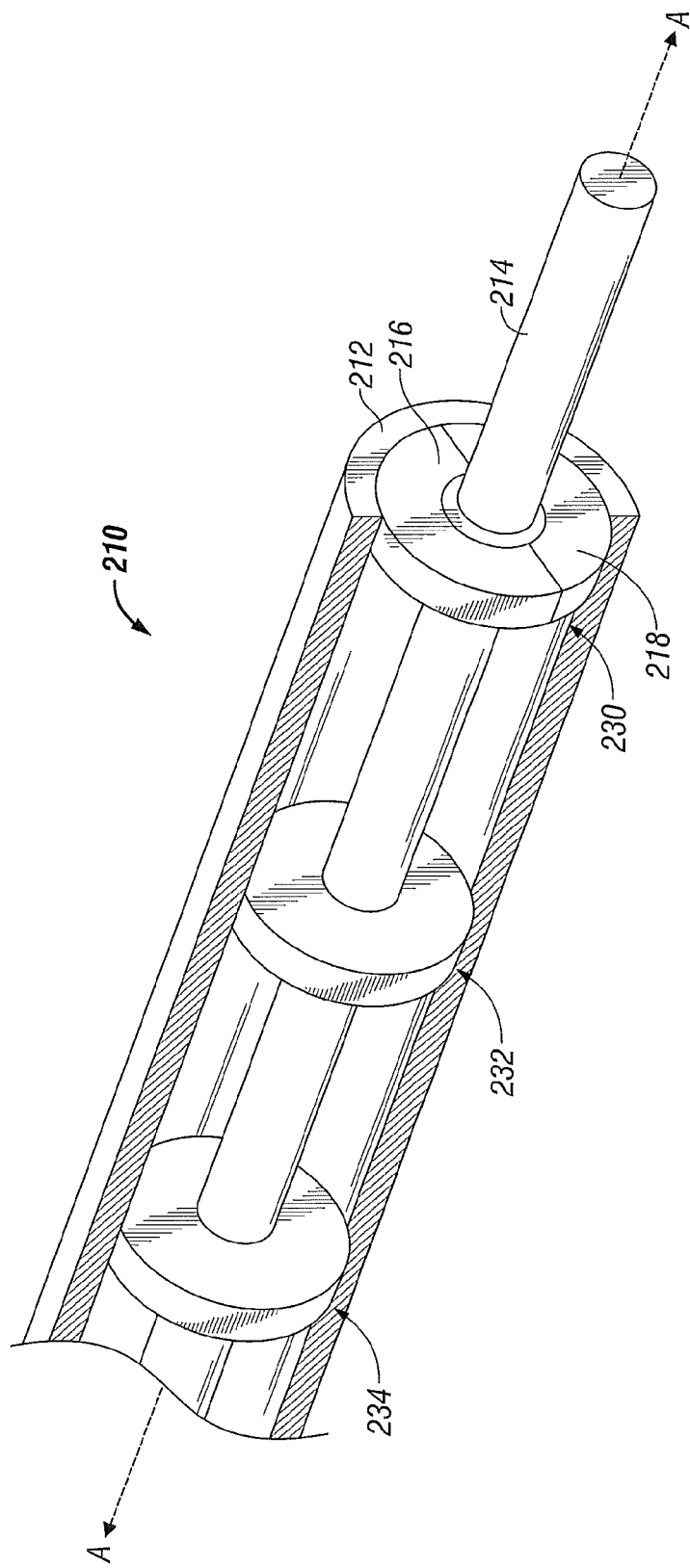
FIG. 3 is a schematically illustrated, cross-sectional view of a coaxial cable having an inner conductor held by one or more spacers being composed of one or more materials having different coefficient of thermal expansion values, in accordance with another embodiment of the present disclosure.

FIG. 3 is a schematically illustrated cross-sectional view of a coaxial cable 210 having an inner conductor 214 held by one or more spacers 230, 232, 234 being composed of one or more materials having different coefficient of thermal expansion values. In FIG. 3, the coaxial cable 210 includes an outer conductor 212, an inner conductor 214, a first material 216, a second material 218, a first spacer 230, a second spacer 232 and a third spacer 234. The inner conductor 214 is connected to an external power source 300.

The first, second, and third spacers 230, 232, 234 maintain a desired position (e.g., a center position) for the inner conductor 214 for at least a partial length of the coaxial cable 210. Each of the spacers 230, 232, 234 may have the same or a different width, and each may be composed of one material or two or more materials. Also, the material used for each spacer may be different. For example, a first spacer 230 may be composed of a first material 216 and a second material 218, whereas the second and third spacers 232, 234 may be composed of one material.

Figure 4A:
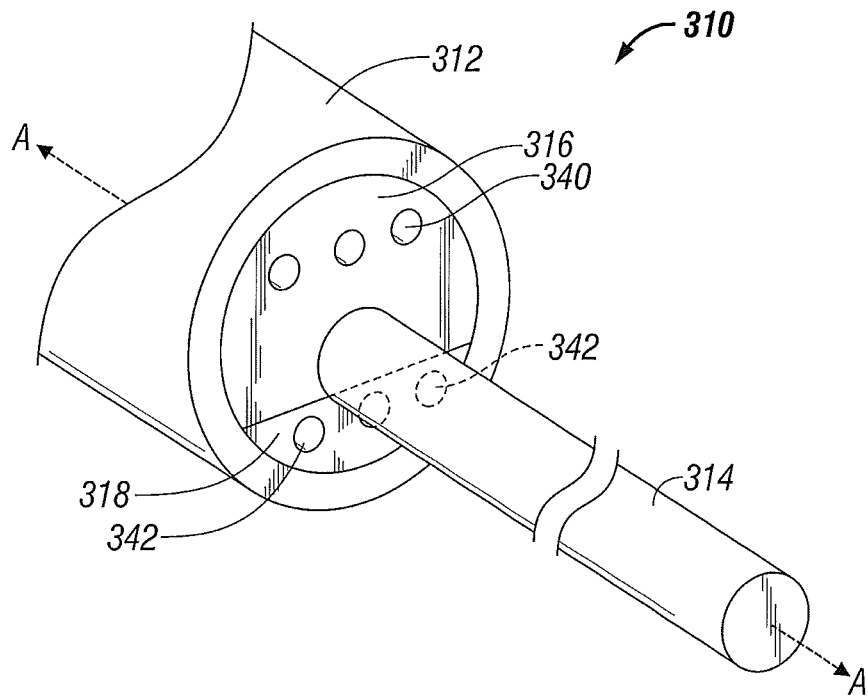
FIG. 4A is a front, perspective view of an off-centered coaxial cable having an inner conductor and a plurality of resistive heating elements in each of two or more materials having different coefficient of thermal expansion values, in accordance with another embodiment of the present disclosure.
Figure 4B:
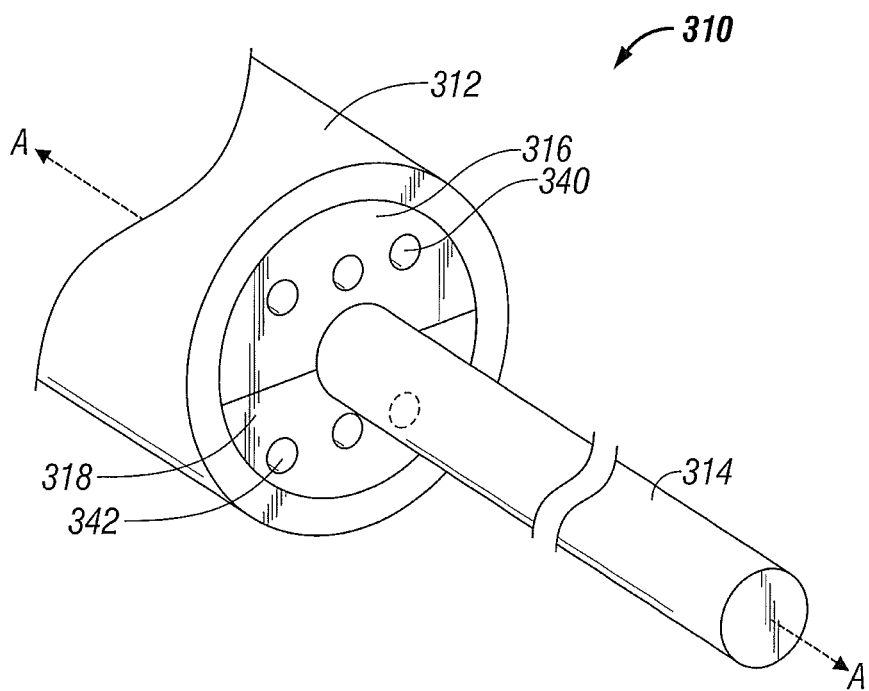
FIG. 4B is a front, perspective view of a centrally disposed coaxial cable having an inner conductor and a plurality of resistive heating elements in each of two or more materials having different coefficient of thermal expansion values, in accordance with another embodiment of the present disclosure.

FIG. 4A is a schematically illustrated cross-sectional view of an off-centered coaxial cable 310 and FIG. 4B is a schematically illustrated cross-sectional view of a centrally disposed coaxial cable 310 having an inner conductor and a plurality of resistive heating elements in each of two or more materials having different coefficient of thermal expansion values. In FIGS. 4A and 4B, the coaxial cable 310 includes an outer conductor 312, an inner conductor 314, a first material 316, a second material 318, first resistive heating elements 340 and second resistive heating elements 342.

FIG. 4A illustrates the inner conductor 314 in an off-centered position within the coaxial cable 310. As heat is applied via the heating resistive elements 340, 342 shown in FIG. 4B, the inner conductor 314 moves to a centered position due to the thermal expansion of material 318. As the tissue impedance changes, the alignment sensitivity of the cable 310 may be selectively changed (e.g., automatically or manually) such that the impedance of the cable 310 better matches the tissue impedance. One or more materials may be utilized to tune the inner conductor 314 according to a desired setting, such as an ohmage setting.

A plurality of first resistive heating elements 340 may be positioned in first material 316 and a plurality of second resistive heating elements 342 may be positioned in second material 318. The first and second resistive heating elements 340, 342 convert electricity into heat. Electrical current running through the elements encounter resistance, thus resulting in heating of the element. Resistive heating elements 340, 342 may be made from Nichrome which has a relatively high resistance and does not break down or oxidize in air at useful temperature ranges. First and second resistive heating elements 340, 342 may also be positioned in parallel to the inner conductor 314, at various lengths from the inner conductor 314, and in various widths. The temperature of each of the plurality of heating elements 340, 342 may be selectively controllable to position the inner conductor 314 relative to the outer conductor 312 and the plurality of heating elements 340, 342 may be disposed in a concentric array relative to the inner conductor 314.

Figure 5A:
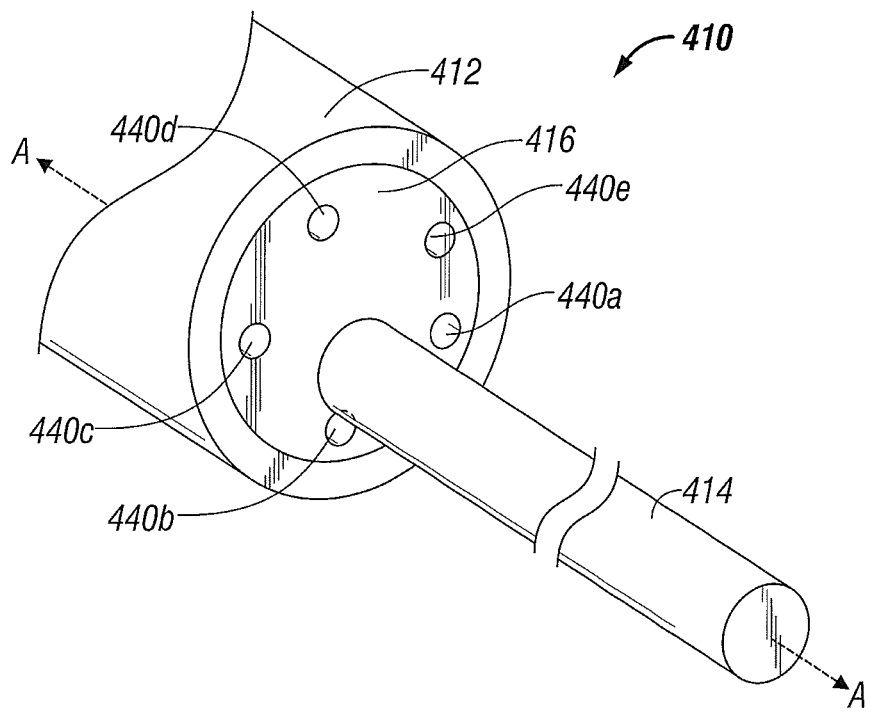
FIG. 5A is a schematically illustrated cross-sectional view of an off-centered coaxial cable having an inner conductor and a plurality of resistive heating elements in one material having one coefficient of thermal expansion value, in accordance with another embodiment of the present disclosure.
Figure 5B:
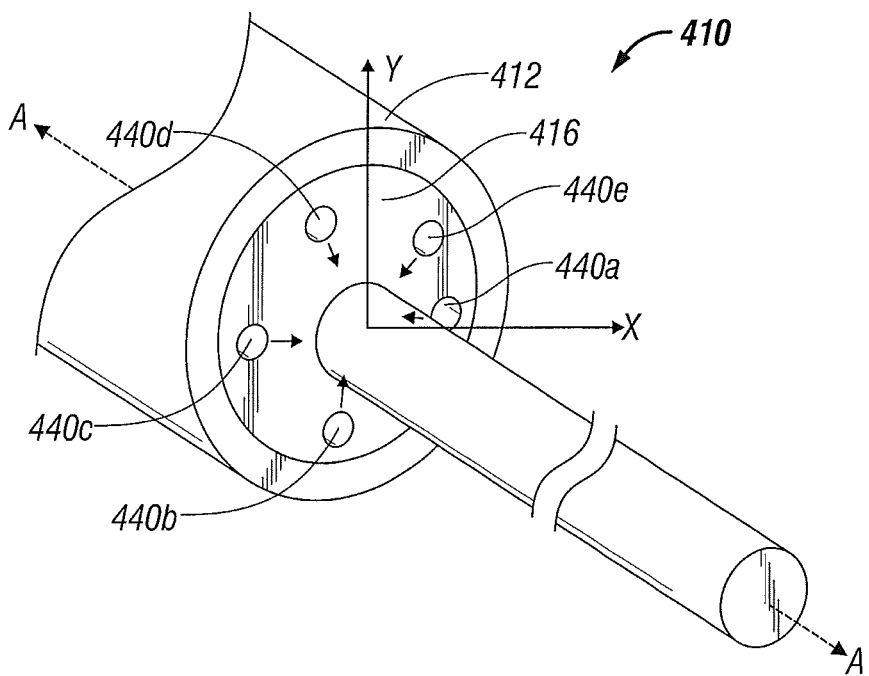
FIG. 5B is a front, perspective view of a centrally disposed coaxial cable having an inner conductor and a plurality of resistive heating elements in one material having one coefficient of thermal expansion value, in accordance with another embodiment of the present disclosure.

FIG. 5A is a schematically illustrated cross-sectional view of an off-centered coaxial cable 410 and FIG. 5B is a schematically illustrated cross-sectional view of a centrally disposed coaxial cable 410. In FIGS. 5A and 5B, the coaxial cable 410 includes an outer conductor 412, an inner conductor 414, a dielectric material 416, and one or more resistive heating elements 440. In contrast to FIGS. 4A and 4B, only one dielectric material 416 is used to surround the entire length of the inner conductor 414. The dielectric material 416 includes one or more resistive heating elements 440 in parallel to the inner conductor 414 along the length of the cable 410. More particularly, the resistive heating elements 440 are positioned in parallel to the inner conductor 414, at various lengths along the inner conductor 414, and in various widths.

FIG. 5A illustrates the inner conductor 414 in an off-centered position within the dielectric material 416. As heat is applied, the inner conductor 414 is moved to a desired position (e.g., a center position) due to the thermal expansion of dielectric material 416 and due to first resistive heating element 440b being heated to expand the dielectric material 416 in a given direction. Any member or combination of heating elements 440a-440e may be utilized to move the inner conductor 414 for tuning purposes. As the tissue impedance changes, the alignment sensitivity of the cable 410 may be selectively changed (e.g., automatically or manually) such that the impedance of the cable 410 better matches the tissue impedance.

Figure 6:
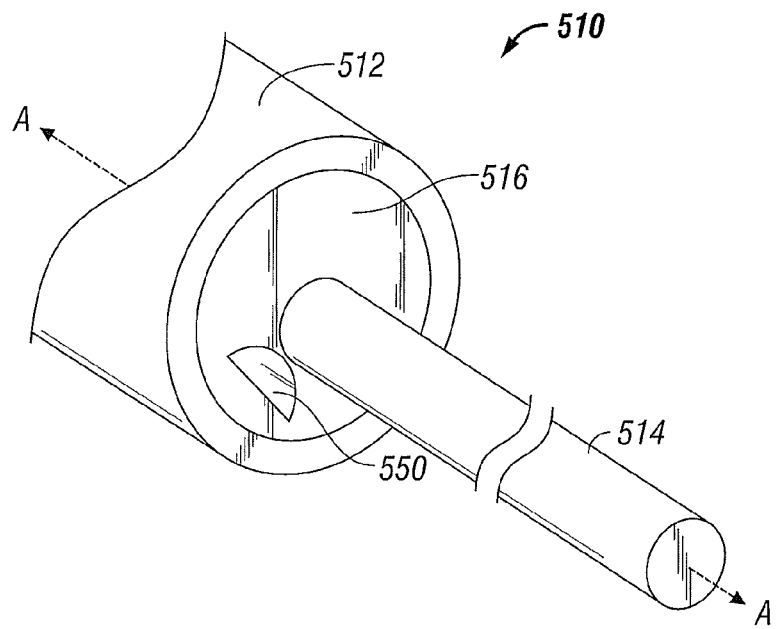
FIG. 6 is a front, perspective view of a coaxial cable having an inner conductor with a shape memory alloy, in accordance with another embodiment of the present disclosure.

FIG. 6 is a schematically illustrated cross-sectional view of a coaxial cable having an inner conductor with a shape memory alloy 550 in accordance with another embodiment of the present disclosure. In FIG. 6, the coaxial cable 510 includes an outer conductor 512, an inner conductor 514, a dielectric material 516 and a shape memory alloy 550.

The shape memory alloy 550 is, for example, positioned in proximity to the inner conductor 514. One or more shape memory alloys 550 may be positioned along the length of the coaxial cable 510 in predetermined distance from each other.

Shape memory alloys (SMAs) are a family of alloys having anthropomorphic qualities of memory and trainability and are particularly well suited for use with medical instruments. SMAs have been applied to such items as actuators for control systems, steerable catheters and clamps. One of the most common SMAs is Nitinol which can retain shape memories for two different physical configurations and changes shape as a function of temperature. Recently, other SMAs have been developed based on copper, zinc and aluminum and have similar shape memory retaining features.

SMAs undergo a crystalline phase transition upon applied temperature and/or stress variations. A particularly useful attribute of SMAs is that after it is deformed by temperature/stress, it can completely recover its original shape on being returned to the original temperature. The ability of an alloy to possess shape memory is a result of the fact that the alloy undergoes a reversible transformation from an austenitic state to a martensitic state with a change in temperature/stress. This transformation is referred to as a thermoelastic martenistic transformation.

Under normal conditions, the thermoelastic martenistic transformation. occurs over a temperature range which varies with the composition of the alloy, itself, and the type of thermal-mechanical processing by which it was manufactured. In other words, the temperature at which a shape is "memorized" by an SMA is a function of the temperature at which the martensite and austenite crystals form in that particular alloy. For example, Nitinol alloys can be fabricated so that the shape memory effect will occur over a wide range of temperatures, e.g., −2700 to +1000 Celsius. Many SMAs are also known to display stress-induced martenisite (SIM) which occurs when the alloy is deformed from its original austenitic state to a martensitic state by subjecting the alloy to a stress condition.

As a result, when heat is applied to the coaxial cable 510, the inner conductor 514 tends to move from its desired position within the coaxial cable 510. SMA 550, which is embedded within a material 516 having a certain coefficient of thermal expansion and which is located in a close proximity to the inner conductor 514 may move the inner conductor 514 back to its desired position (e.g., a center position) within the coaxial cable 510. SMA 550 can recover from large amounts of bending and torsional deformations, due to the application of heat, as well as small amounts of strain. Provided the deformations are within recoverable ranges, the process of deformation and shape recovery can be repeated millions of times. As a result, the SMA 550 located within the material 516 can repeatedly move the inner conductor 514 back to a desired position (e.g., a centered position). Moreover, as can be appreciated, the material 516 may be designed to selectively (e.g., either automatically or manually) align or misalign the inner conductor 514 relative to the outer conductor 512 for tuning and impedance matching purposes.

Consequently, the embodiments of the present disclosure allow for improved antenna impedance matching for controlling tissue impedance of a microwave antenna during an ablation procedure via a thermally tuned coaxial cable. The embodiments further include changing the impedance of the coaxial cable for allowing greater flexibility in designing microwave antennas. By having a varying impedance of the coaxial cable in the antenna tuned to change with the increase/decrease in temperature, tissue impedance changes, and thus, the antenna may deposit a greater amount of energy over the entire course of the ablation procedure. By using dielectric cores of varying thermal expansion values, it is possible to force the eccentricity of the inner conductor of the coaxial cable on-line or off-line, thus effectively changing the coaxial cable's impedance value.

In addition, FIGS. 1A-2D illustrate two materials 16, 18 within the spacing between the inner surface of the outer conductor 12 and the outer surface of the inner conductor 14 including two air spaces or gaps 20, 22. However, one skilled in the art may use more than two materials within the spacing between the inner surface of the outer conductor 12 and the outer surface of the inner conductor 14 and more than two air gaps. For example, one skilled in the art may be motivated to use three or more materials, each with a different coefficient of thermal expansion value in a triangular configuration with three or more air gaps separating the materials. In addition, one skilled in the art may be motivated to use two materials in a checkered pattern or any other type of intertwined pattern with one or more air gaps in order to center or off-center the inner conductor 14 of the coaxial cable 10 as needed to tune or match the tissue impedance.

Further, in FIGS. 1A-6 there may be one or more mechanisms that regulate the thermal expansion of at least one of the first and second dielectric materials 16, 18 to position the inner conductor 14 relative to the outer conductor 12 to change the impedance of the inner conductor 14.

Figure 7:
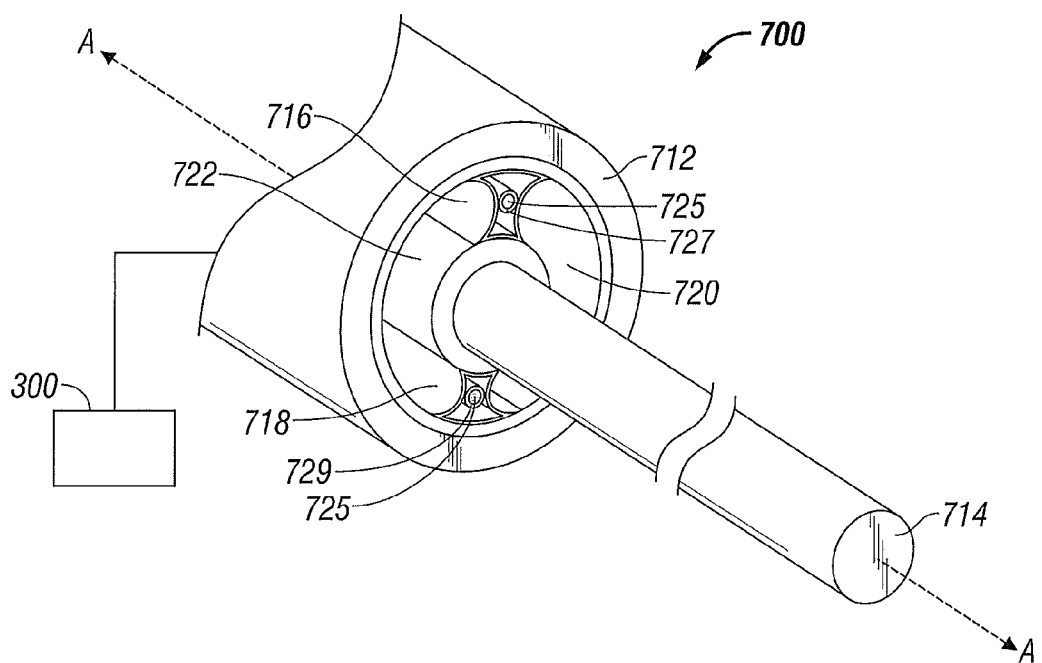
FIG. 7 is a front, perspective view of a centrally-disposed coaxial cable having an inner conductor held by two materials having different coefficient of thermal expansion values with a fluid circulated therethrough for regulating the thermal expansion of the two materials in accordance with another embodiment of the present disclosure.

FIG. 7 shows another embodiment according to the present disclosure wherein the coaxial cable 700 includes an outer conductor 712 arranged to be generally concentric with respect to the inner conductor 714 used for transmitting signals. Inner conductor 714 is held relative to the outer conductor 712 by first material 716 and second material 718 only one of which contacts inner conductor 714. First material 716 and the second material 718, respectively, define first and second air gaps 720 and 722, between the inner surface of the outer conductor 712 and the outer surface of the inner conductor 714. A fluid 725 is circulated within one or both the first and second dielectric materials 716, 718 via conduits 727 and 729 defined respectively therein. The relative temperature of the fluid 725 may be selectively controllable via circuitry controlled by the generator 300 to regulate thermal expansion of one or both the first and second dielectric materials 716, 718 to position the inner conductor 714 relative to the outer conductor 712 to change the impedance of the inner conductor 714. The fluid 725 may optionally or alternatively be disposed between the first and second dielectric materials 716, 718 and be controlled in a similar manner.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

What is claimed is:

1. A coaxial cable, comprising:
    an inner conductor;
    an outer conductor surrounding the inner conductor, the inner conductor in general concentric alignment with the outer conductor, the inner and outer conductors adapted to each connect to an energy source; and
    a thermally responsive material disposed between the inner and outer conductors;
    wherein a change in temperature of the thermally responsive material alters the concentric alignment of the inner and outer conductors.

2. The coaxial cable according to claim 1, wherein the thermal responsive material positioned between the inner and outer conductors is a dielectric.

3. The coaxial cable according to claim 1, wherein the thermally responsive material includes:
    a first thermally responsive material that surrounds the inner conductor; and
    a plurality of resistive heating elements disposed in the first thermally responsive material and substantially parallel to the inner conductor along a length of the coaxial cable,
    wherein the concentric alignment of the inner and outer conductors is determined by the application of heat to the first dielectric material via the one or more of the plurality of resistive heating elements.

4. The coaxial cable according to claim 1, wherein the thermally responsive material includes a shape memory alloy responsive to changes in temperature wherein a thermal change in the shape memory alloy alters the concentric alignment of the inner and outer conductors.

5. The coaxial cable according to claim 1, wherein the thermally responsive material includes a plurality of spacers in a longitudinally spaced apart relationship with respect to each other.

6. The surgical device of claim 1, wherein the thermally responsive material is selectively configurable via the application of heat to alter the concentric alignment of the inner conductor relative to the outer conductor for tuning and impedance matching.

7. The surgical device of claim 1, wherein the thermally responsive material is selectably configurable via the application of heat to position the inner conductor relative to the outer conductor from a first position wherein the inner conductor is concentrically aligned with the outer conductor to a second position wherein the inner conductor is not concentrically aligned with the outer conductor.

8. The coaxial cable according to claim 1, wherein the thermally responsive material is selected from the group consisting of ABS Polymer Extruded, ABS Polymer Nylon Blend, PEKK Polyketone, PEEK Polyketone, Nylon PTFE Filled, Polycarbonate Extruded, LDPE (Polyethylene), Polyimide, PTFE Molded, Silica Aerogel and combinations thereof.

9. The coaxial cable according to claim 1, wherein the coaxial cable includes a sensor that monitors at least one of the inner and outer conductors for determining the position of the inner conductor relative to the outer conductor.

10. A coaxial cable, comprising:
an inner conductor; and
an outer conductor surrounding the inner conductor, the inner conductor in general concentric alignment with the outer conductor, the inner and outer conductors each adapted to connect to an energy source, wherein the impedance of the coaxial cable is related to the eccentricity of the inner conductor relative to the outer conductor which is responsive to a change in temperature.

11. A coaxial cable, comprising:
an inner conductor;
an outer conductor surrounding the inner conductor, the inner and outer conductors each adapted to connect to an energy source;
a dielectric material disposed between the inner and outer conductors; and
a mechanism coupled to the dielectric material configured to regulate the dielectric material to position the inner conductor relative to the outer conductor.

12. The coaxial cable according to claim 11, wherein the mechanism is selected from a shaped memory alloy and a heat resistive element.

* * * * *